(12) United States Patent
Fischell et al.

(10) Patent No.: US 7,060,088 B1
(45) Date of Patent: Jun. 13, 2006

(54) STENT WITH IMPROVED FLEXIBLE CONNECTING LINKS

(75) Inventors: Robert E. Fischell, Dayton, MD (US); David R. Fischell, Fair Haven, NJ (US); David C. Majercak, Flemington, NJ (US)

(73) Assignee: Cordis Corporation, Miami Lakes, FL (US)

( * ) Notice: Subject to any disclaimer, the term of this patent is extended or adjusted under 35 U.S.C. 154(b) by 943 days.

(21) Appl. No.: 09/609,163

(22) Filed: Jun. 30, 2000

Related U.S. Application Data (63) Continuation of application No. 09/192,101, filed on Nov. 13, 1998, now Pat. No. 6,190,403.

(51) Int. Cl.
*A61F 2/06* (2006.01)

(52) U.S. Cl. ................................... 623/1.15

(58) Field of Classification Search ...... 623/1.11–1.22; 606/108, 191, 192, 194, 195, 198
See application file for complete search history.

(56) References Cited

U.S. PATENT DOCUMENTS

| 3,657,744 A | 4/1972 | Ersek |
| 4,441,216 A | 4/1984 | Ionescu et al. ............... 3/1.5 |
| 4,503,569 A | 3/1985 | Dotter |
| 4,553,545 A | 11/1985 | Maass et al. |
| 4,580,568 A | 4/1986 | Gianturco ............... 128/345 |
| 4,733,665 A | 3/1988 | Palmaz |
| 4,776,337 A | 10/1988 | Palmaz |
| 4,800,882 A | 1/1989 | Gianturco ............... 128/343 |
| 4,856,516 A | 8/1989 | Hillstead ............... 128/343 |
| 4,886,062 A | 12/1989 | Wiktor ............... 128/343 |
| 4,907,336 A | 3/1990 | Gianturco ............... 29/515 |
| 4,969,458 A | 11/1990 | Wiktor ............... 606/194 |
| 4,990,131 A | 2/1991 | Dardik ............... 600/36 |
| 4,990,155 A | 2/1991 | Wilkoff ............... 606/191 |
| 4,994,071 A | 2/1991 | MacGregor ............... 606/194 |
| 5,015,253 A | 5/1991 | MacGregor ............... 623/1 |
| 5,035,706 A | 7/1991 | Gianturco ............... 606/198 |
| 5,041,126 A | 8/1991 | Gianturco ............... 606/195 |
| 5,064,435 A | 11/1991 | Porter ............... 623/12 |
| 5,102,417 A | 4/1992 | Palmaz |
| 5,104,404 A | 4/1992 | Wolff ............... 612/1 |
| 5,116,365 A | 5/1992 | Hillstead ............... 623/1 |

(Continued)

FOREIGN PATENT DOCUMENTS

DE 3205942 A1 9/1983

(Continued)

*Primary Examiner*—Vy Bui (57) ABSTRACT

Disclosed is a stent that has flexible connecting links that have a strut width as measured in a direction that is generally along the surface of the stent that is smaller than the wall thickness of the stent as measured in a radial direction from the stent's longitudinal axis. The strut width for a coronary stent should be less than 0.10 mm to provide good flexibility while the wall thickness should be greater than 0.10 mm to provide good stent radiopacity. Ideally the ratio of the width to the thickness should be less than 1.0 and preferably less than 0.08 mm and the nominal wall thickness would typically be 0.12 mm. The combination of thin strut width and thick wall thickness will allow the flexible link to easily lengthen and shorten for increased stent flexibility while making the link relatively stiff with respect to bulging inward into the lumen of the stent. This stiffness enhances the ability of the link to push outward against plaque in a coronary artery after the stent is deployed. In addition to improved flexibility, the thin width of the flexible links allow them to stretch during stent expansion thus reducing foreshortening of the deployed stent.

5 Claims, 8 Drawing Sheets

U.S. PATENT DOCUMENTS

| | | | | |
|---|---|---|---|---|
| 5,122,154 | A | 6/1992 | Rhodes | 606/198 |
| 5,131,908 | A | 7/1992 | Dardik et al. | 600/36 |
| 5,133,732 | A | 7/1992 | Wiktor | 606/195 |
| 5,135,536 | A | 8/1992 | Hillstead | 606/195 |
| 5,163,958 | A | 11/1992 | Pinchuk | 623/11 |
| 5,171,262 | A | 12/1992 | MacGregor | 623/1 |
| 5,176,660 | A | 1/1993 | Truckai | 604/282 |
| 5,178,618 | A | 1/1993 | Kandarpa | 606/28 |
| 5,192,307 | A | 3/1993 | Wall | 623/1 |
| 5,195,984 | A | 3/1993 | Schatz | |
| 5,217,483 | A | 6/1993 | Tower | 606/198 |
| 5,222,971 | A | 6/1993 | Willard et al. | 606/158 |
| 5,246,445 | A | 9/1993 | Yachia et al. | 606/108 |
| 5,258,021 | A | 11/1993 | Duran | 623/2 |
| 5,266,073 | A | 11/1993 | Wall | 623/1 |
| 5,275,622 | A | 1/1994 | Lazarus et al. | 623/1 |
| 5,282,823 | A | 2/1994 | Schwartz et al. | 606/198 |
| 5,282,824 | A | 2/1994 | Gianturco | 606/198 |
| 5,290,305 | A | 3/1994 | Inoue | |
| 5,292,331 | A | 3/1994 | Boneau | 606/198 |
| 5,304,200 | A | 4/1994 | Spaulding | 606/198 |
| 5,314,444 | A | 5/1994 | Gianturco | 606/195 |
| 5,314,472 | A | 5/1994 | Fontaine | 623/12 |
| 5,334,301 | A | 8/1994 | Heinke et al. | 204/267 |
| 5,342,387 | A | 8/1994 | Summersq | 606/198 |
| 5,354,257 | A | 10/1994 | Roubin et al. | 600/7 |
| 5,354,308 | A | 10/1994 | Simon et al. | 606/198 |
| 5,366,504 | A | 11/1994 | Andersen et al. | 623/11 |
| 5,370,683 | A | 12/1994 | Fontaine | 623/1 |
| 5,370,691 | A | 12/1994 | Samson | 623/12 |
| 5,375,612 | A | 12/1994 | Cottenceau et al. | 128/899 |
| 5,376,112 | A | 12/1994 | Duran | 623/2 |
| 5,382,261 | A | 1/1995 | Palmaz | 606/198 |
| 5,387,235 | A | 2/1995 | Chuter | 623/1 |
| 5,389,106 | A | 2/1995 | Tower | 606/198 |
| 5,395,390 | A | 3/1995 | Simon et al. | 606/198 |
| 5,397,355 | A | 3/1995 | Marin et al. | 623/12 |
| 5,403,341 | A | 4/1995 | Solar | 606/198 |
| 5,405,377 | A | 4/1995 | Cragg | 623/1 |
| 5,411,549 | A | 5/1995 | Peters | 623/1 |
| D359,802 | S | 6/1995 | Fontaine | D24/155 |
| 5,421,955 | A | 6/1995 | Lau et al. | |
| 5,423,885 | A | 6/1995 | Williams | 623/1 |
| 5,441,515 | A | 8/1995 | Khosravi et al. | 606/194 |
| 5,441,516 | A | 8/1995 | Wang et al. | 606/198 |
| 5,443,477 | A | 8/1995 | Marin et al. | 606/198 |
| 5,443,496 | A | 8/1995 | Schwartz et al. | 623/1 |
| 5,443,498 | A | 8/1995 | Fontaine | 623/1 |
| 5,443,500 | A | 8/1995 | Sigwart | 623/1 |
| 5,449,372 | A | 9/1995 | Schmaltz et al. | 606/198 |
| 5,449,373 | A | 9/1995 | Pinchasik et al. | |
| 5,449,382 | A | 9/1995 | Dayton | 623/1 |
| 5,496,365 | A | 3/1996 | Sgro | |
| 5,527,354 | A | 6/1996 | Fontaine et al. | |
| 5,569,295 | A | 10/1996 | Lam | |
| 5,591,197 | A | 1/1997 | Orth et al. | |
| 5,632,763 | A | 5/1997 | Glastra | 606/194 |
| 5,643,312 | A | 7/1997 | Fischell et al. | 606/198 |
| 5,649,952 | A | 7/1997 | Lam | |
| 5,653,747 | A | 8/1997 | Dereume | 623/1 |
| 5,669,924 | A | 9/1997 | Shaknovich | 606/108 |
| 5,697,971 | A | 12/1997 | Fischell et al. | |
| 5,733,303 | A | 3/1998 | Israel et al. | 606/198 |
| 5,755,734 | A | 5/1998 | Richter et al. | 606/194 |
| 5,800,508 | A | 9/1998 | Goicoechea et al. | 623/1 |
| 5,807,404 | A * | 9/1998 | Richter | 623/1 |
| 5,836,964 | A | 11/1998 | Richter et al. | 606/194 |
| 5,843,120 | A | 12/1998 | Israel et al. | 606/198 |
| 5,861,027 | A | 1/1999 | Trapp | 623/1 |
| 5,913,895 | A | 6/1999 | Burpee et al. | |
| 5,935,162 | A | 8/1999 | Dang | |
| 5,972,018 | A | 10/1999 | Israel et al. | 606/198 |
| 6,001,123 | A | 12/1999 | Lau | |
| 6,017,365 | A | 1/2000 | Von Oepen | |
| 6,019,789 | A | 2/2000 | Dinh et al. | |
| 6,033,435 | A | 3/2000 | Penn et al. | |
| 6,059,811 | A | 5/2000 | Pinchasik et al. | 606/198 |
| 6,129,754 | A | 10/2000 | Kanesaka et al. | |
| 6,171,334 | B1 | 1/2001 | Cox | |
| 6,179,867 | B1 | 1/2001 | Cox | |
| 6,193,747 | B1 | 2/2001 | Von Oepen | |
| 6,217,608 | B1 | 4/2001 | Penn et al. | |
| 6,231,598 | B1 | 5/2001 | Berry et al. | |

FOREIGN PATENT DOCUMENTS

| | | |
|---|---|---|
| EP | 0 540 290 A2 | 10/1992 |
| EP | 0734698 A2 | 3/1996 |
| EP | 0800801 A1 | 8/1996 |
| EP | 0830853 A1 | 7/1997 |
| EP | 0 540 290 A3 | 10/1999 |
| FR | 0 566 807 A1 | 4/1992 |
| GB | 1 205 743 | 9/1970 |
| GB | 0 662 307 A2 | 12/1994 |
| JP | 6-41745 | 6/1994 |
| WO | WO96/26689 | 9/1996 |
| WO | WO 96/34580 | 11/1996 |
| WO | WO97/25000 | 7/1997 |
| WO | WO-98-40 * | 3/1998 |
| WO | WO 98/19628 | 5/1998 |
| WO | WO 00/62710 | 10/2000 |
| WO | WO00/62710 A1 | 10/2000 |

* cited by examiner

FIG. 1

"PRIOR ART"

STENT WITH IMPROVED FLEXIBLE CONNECTING LINKS

This is continuation of application Ser. No. 09/192,101 filed Nov. 13, 1998 now U.S. Pat. No. 6,190,403.

FIELD OF USE

The present invention is an expandable stent for insertion into a vessel of a human body for the purpose of creating and maintaining the patency of that vessel.

BACKGROUND

In U.S. Pat. No. 5,697,971 Fischell et al describe a balloon expandable stainless steel vascular stent with two different cell types. Cells containing an "H"-shaped link to provide strength and cells having an "S"-shaped link to provide increased flexibility and the ability to "unjail" side branch arteries. In addition, "S" links of the Fischell, et al invention attach to the strut members at the center of the end of the end struts. This increases the length of the "S" link along the longitudinal axis of the stent as compared with off-center attachment points. Finally, the "H" link of the Fischell et al prior art stent increases the relative strength of the section of the stent where it is used by shortening the distance between adjacent sets of strut members as compared to the distance between adjacent strut members for the "S" links.

SUMMARY OF INVENTION

The current invention is a comparatively thick-walled vascular stent comprising sets of strut members connected by flexible links. This design uses a script "N" shaped flexible link instead of the "S" link described by Fischell et al in U.S. Pat. No. 5,697,971. The "N" links, instead of touching or overlapping during crimping, are designed to nest one into the other, allowing the stent to be both thick-walled and to crimp down without overlap onto a low profile balloon. The "N" links are attached to the strut members not at the center like the "S" links in the prior art, but off center near the end of the curved end strut portion of each strut member. This off center attachment point allows for a more flexible link without increasing the cell size of the expanded stent. Small cell size is desirable to limit plaque prolapse into the lumen of the expanded stent. It is also desirable to replace the "H" link described by Fischell et al in the prior art with a short "J"-shaped, flexible link that will keep the struts close together for strength but unlike the "H" link will not detract from the stent's flexibility. To enhance flexibility, the wire width of the "N" and "J" links should be less than 0.10 mm. The relatively thin strut width with thick wall allows the "J" and "N" links to easily lengthen and shorten during stent delivery into the body while still allowing the stent to retain a considerable degree of radial strength.

An alternative embodiment of the flexible thick-walled stent has also been envisioned where the "N" link has certain curved segments to further minimize stent cell size. It is also conceived to increase flexibility by using "M"-shaped or "W"-shaped links each having additional undulations as compared to the "W" link.

Thus an object of this invention is to have a multi-cell, thick-walled stent with at least two different types of closed perimeter cells where every cell includes at least one longitudinally extending flexible link.

Another object of this invention is to have a stent with flexible links designed to nest inside each other when the stent is crimped down onto the balloon of a balloon catheter so as to reduce the stent profile (i.e., to reduce the outer diameter).

Another object of this invention is to have a stent with flexible links having the shapes of a "J", inverted "J", an "N", inverted "N", a sine wave, "M" or "W".

Another object of this invention is to have a stent with flexible links that are attached off center to the curved ends of the strut members.

Still another objective of this invention is to have a multi-cell stent with short flexible links forming the part of the perimeter of one type of cell and longer flexible links forming part of the perimeter of a second type of cell.

Still another objective of this invention is to have a thick-walled stent with "N" shaped links where two of the three vertical segments of the "N" are curved to minimize the longitudinal extent of the link and thus minimize cell size for the expanded stent.

Still another object of this invention is to have flexible links between sets of strut members where the ratio of link width to link wall thickness is less than 1.0.

Still another object of this invention is to have the struts at the ends of the stent be of a shorter length as compared to struts at a central location so as to enhance the radial strength at the ends of the stent.

Still another objective of this invention is to have a stent in which the sets of strut members are constructed from several connected arcs of different radii with no straight segments.

Still another objective of this invention is to have a stent adapted for implantation at the ostium of a vessel, the stent having an extremely flexible distal section and a less flexible proximal section, the proximal section being radially stronger than the distal section after stent expansion to its nominal diameter.

These and other important objects and advantages of this invention will become apparent from the detailed description of the invention and the associated drawings provided herein.

DETAILED DESCRIPTION OF THE INVENTION

Figure 1:
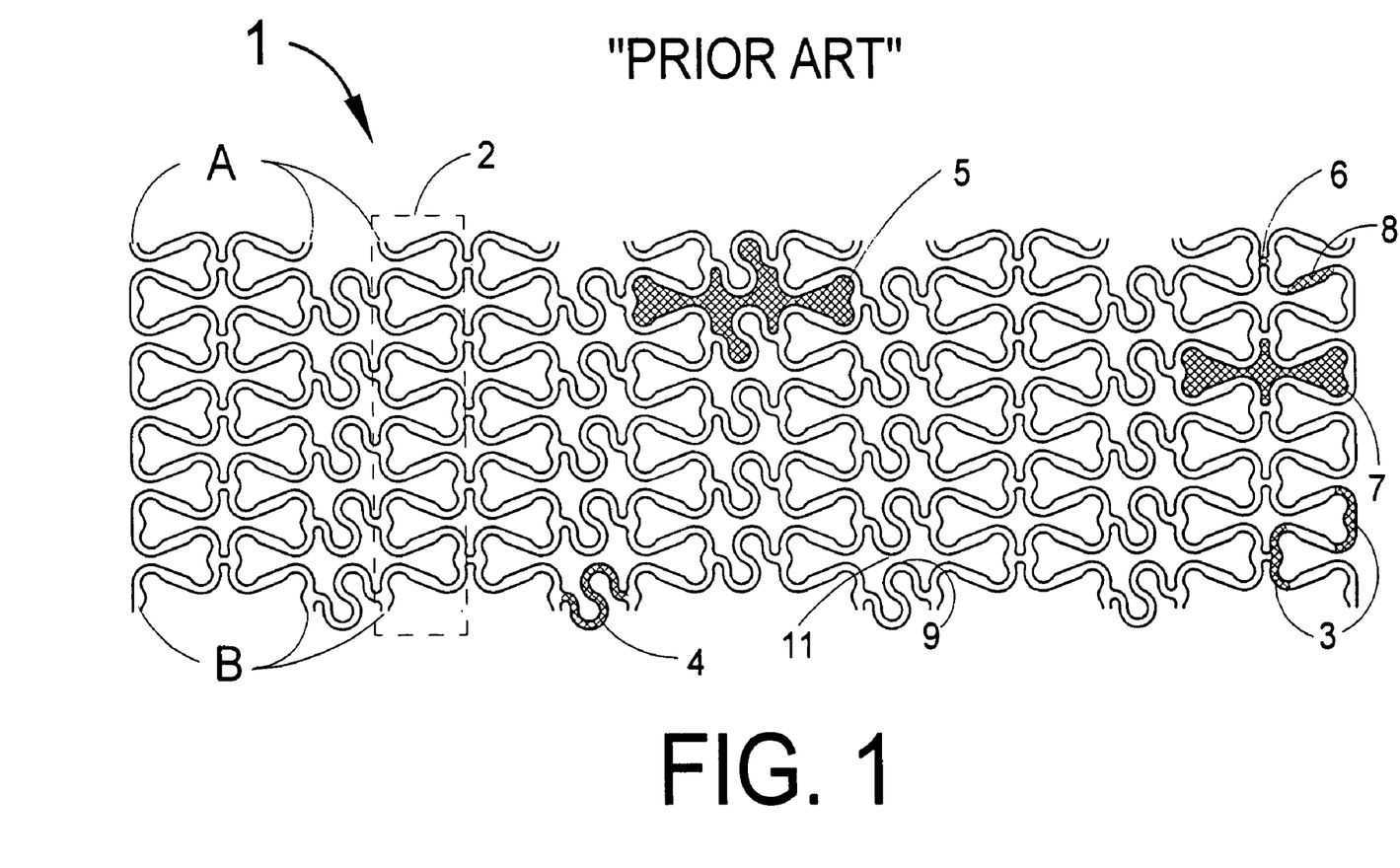
FIG. 1 a flat, layout, 2-dimensional plan view of a prior art cylindrical stent in its pre-deployed state.

FIG. 1 shows a prior art stent 1 as it would appear if it were cut longitudinally and then laid out into a flat, 2-dimensional configuration. It should be clearly understood that the stent 1 is in fact cylindrical in shape, which cylindrical shape would be obtained by rolling the flat configuration of FIG. 1 into a cylinder with the top points "A" joined to the bottom points "B". The stent 1 is typically fabricated by laser machining of a thin-walled, cylindrical, stainless steel tube.

The stent 1 has exactly two different types of cells: namely, structural cells 7 and special expandable cells 5. Both these cells are formed from end struts 3 and diagonal struts 8. The horizontal "H" links 6 form part of the perimeter of the cells 7. The undulating "S" links 4 form part of the perimeter of the expandable cells 5. Within the dotted lines of FIG. 1 is a set of strut members 2, which is a closed, ring-like, cylindrical segment of the stent 1 consisting of a set of connected end struts 3 and diagonal struts 8. The stent 1 also has adjacent sets of strut members 2 that are connected either by multiple "H" links 6 or by multiple "S" links 4. A limitation of the prior art stent 1 is that in crimping the stent 1 down to the small diameters associated with low profile balloons on balloon delivery catheters, the top 9 of one "S" link 4 will come into contact with the bottom 11 of the "S" link 4 that is situated just above the "S" link 4. This may either limit the ability of the stent 1 to crimp further down when the "S" links 4 touch, or will cause the "S" links 4 to overlap. In thin-walled stents with wall thickness less than 0.08 mm, it may be acceptable for the "S" links to overlap, but as wall thickness increases to 0.10 mm and beyond, overlapping is much less acceptable. This is because the overlapped struts will increase the outside diameter (i.e., the profile) of the non-deployed stent as crimped onto a balloon. In stents of wall thickness of 0.12 mm (known to be a wall thickness for stainless steel stents that provides good radiopacity under fluoroscopy), it is desirable to have a flexible link with a shape that will not touch or overlap as the stent is crimped down on low profile balloons.

The rigid "H" link 6 of the stent 1 which is designed to reduce the separation of adjacent sets of strut members 2 for increased radial strength, limits the flexibility of the stent 1 and the ability of each set of strut members 2 to expand independently.

Figure 2:
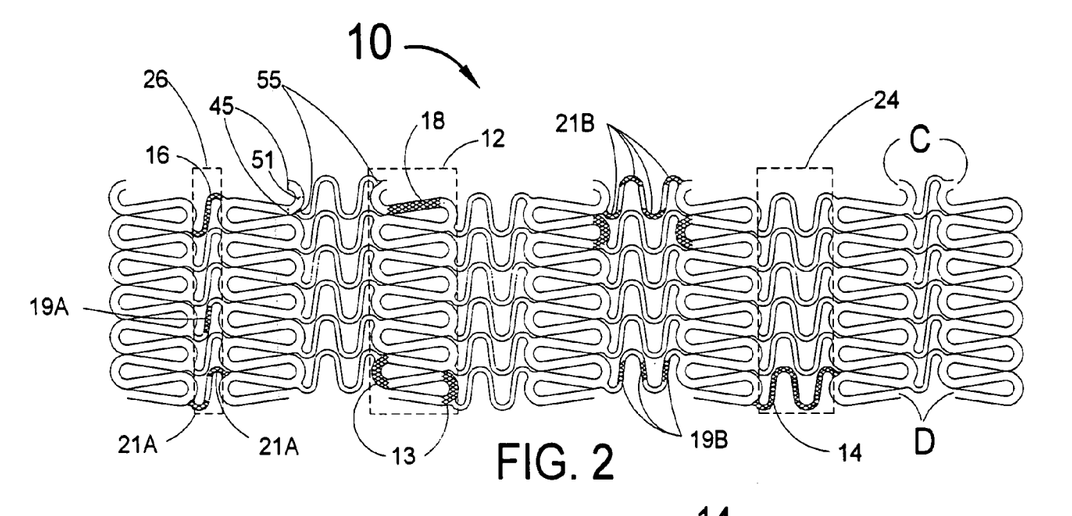
FIG. 2 illustrates one embodiment of the present invention represented as a flat, layout, 2-dimensional plan view of a multi-cell cylindrical stent in its pre-deployed state.

FIG. 2 illustrates one embodiment of the present invention which is the stent 10 in its crimped, pre-deployed state as it would appear if it were cut longitudinally and then laid out into a flat, 2-dimensional configuration. It should be clearly understood that the stent 10 is in fact cylindrical in shape, which cylindrical shape would be obtained by rolling the flat configuration of FIG. 2 into a cylinder with the top points "C" joined to the bottom points "D". The stent 10 is typically fabricated by laser machining of a cylindrical, stainless steel tube.

A set of strut members 12 (as shown within the dotted rectangle 12) is a closed, cylindrical, ring-like section of the stent 10 comprising six pairs of longitudinally separated curved end struts 13 connected by diagonal struts 18. Although the set of strut members 12 consists of twelve curved end struts 13 connected to twelve diagonal struts 18, it is envisioned that embodiments of the present invention stent can be constructed using sets of strut members with as few as eight curved end struts 13 with eight diagonal struts 18, or as many as twenty-four curved end struts 13 with as many as twenty-four diagonal struts 18. The set of strut members can be said to consist of a multiplicity of strut elements with each strut element consisting of one curved end strut 13 joined to one diagonal strut 18.

Except at the extreme ends of the stent, every curved end strut 13 is attached to a connecting link that is either an "N" link 14 or a "J" link 16.

A stent 10 that is thus fully connected is called a "closed cell" stent. Another way to describe the fully connected configuration of the stent 10 is as multiple longitudinally spaced sets of strut members 12 inter-connected by either sets of flexible "N" links 24 or sets of flexible "J" links 26. Each set of flexible "N" links 24 comprising multiple circumferentially spaced "N" links 14 with each "N" link 14 being connected to two curved end struts 13 of adjacent sets of strut members 12. The number of "N" links 14 in the set of "N" links 24 is one-half of the total number of curved end struts 13 in the set of strut members 12. Each set of flexible "J" links 26 consists of multiple circumferentially spaced "J" links 16 with each "J" link being connected to two curved end struts 13 of the adjacent sets of strut members 12. The number of "J" links 16 in the set of "J" links 26 is one half of the total number of curved end struts 13 in the set of strut members 12.

As seen in FIG. 2, each "N" link 14 consists of four generally longitudinally extending curved segments 21B connected by three generally straight circumferentially extending segments 19B. Each "J" link 16 consists of two generally longitudinally extending curved segments 21A connected by a straight circumferential segment 19A.

The stent 10 can be described as having adjacent sets of strut members 12 that are connected either by multiple "N" links 14 or by multiple "J" links 16. Each "N" link 14 is shaped so as to nest together into the adjacent "N" link 14 as is clearly seen in FIG. 2. "Nesting" is defined as having the top of a first flexible link inserted beyond the bottom of a second flexible link that is situated just above that first flexible link and the bottom of that first flexible link is inserted just below the top of a third flexible link that is situated just below that first flexible link. Thus, a stent with nested individual flexible links has each individual flexible link nested into both adjacent flexible links; i.e., the flexible link directly below and the flexible link directly above that individual flexible link. This nesting permits crimping of the stent 10 to smaller diameters than the prior art stent 1 of FIG. 1 without having the "N" links 14 overlap. In the embodiment of FIG. 2, the curved end struts 13 of the sets of strut members 12 are designed so that they touch as shown in FIG. 2 when the adjacent flexible links 14 or 16 are nested within each other. The pre-deployed stent 10 bends easily as it goes around curved arteries because the "N" links 14 can easily lengthen on the outside of the bent stent and shorten on the inside of the bent stent. Each curved end strut 13 of FIG. 2 is shaped like a half-annulus with an arc center 51 and two ends 45. The attachment point 55 for the "N" link 14 to the curved end strut 13 is not at the center point 51 of the curved end strut 13 but at a location between the center point 51 and the end point 45 of the curved end strut 13. This allows each and every generally circumferential segment 19B of the "N" links 14 to be made longer than if the attachment point was near the center point 51 of the curved end struts 13. The longer the circumferential segment 19B of the "N" link 14, the more lever arm will be available to allow flexure of the "N" link 14. This provides improved stent flexibility that is an advantage of this design. It should be noted that the circumferential segments 19B are all of approximately the same length. It should also be noted that each end point 45 of the curved end strut 13 is the junction point where each diagonal strut 18 is joined to each curved end strut 13.

By replacing the "H" link 6 of the prior art stent 1 of FIG. 1 with the "J" link 16 of FIG. 2, there is enough flexure between the sets of strut members 12 connected by the "J" links 16 to permit each to expand independently. The "J" links 16 serve the same purpose as the "H" links 6 of FIG. 1. That purpose being to fully connect adjacent sets of strut members 12 so that the adjacent sets of strut members 12 are longitudinally close to one another thus providing smaller expanded cells and increased radial strength to each end of the stent. Each "J" link 16 has two longitudinally extending curved segments 21A that are joined to one generally circumferentially extending segment 19A.

Figure 3:
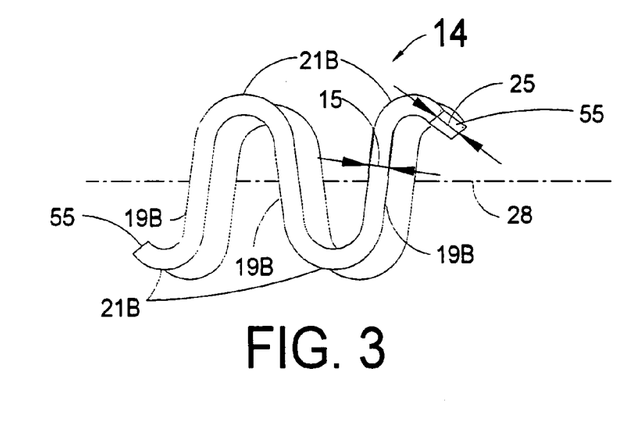
FIG. 3 is a 3-dimensional, perspective view of a flexible "N" link of the stent shown in FIG. 2.

FIG. 3 is a 3-dimensional, perspective view of the flexible "N" link 14 of the stent 10 of FIG. 2. As seen in FIGS. 2 and 3, the "N" link 14 comprises four generally longitudinally extending curved segments 21B connected by three generally circumferentially extending segments 19B with each "N" link 14 having two ends that are identically the attachment point 55 where the "N" link 14 connects to the curved end strut 13. The "N" link 14 shown in FIG. 3 has a strut width 15 as measured in a direction that is generally along the surface of the stent that is smaller than the wall thickness 25 as measured in a radial direction from the stent's longitudinal axis 28. The strut width 15 for a coronary stent should be less than 0.10 mm to provide good flexibility while the wall thickness 25 should be greater than 0.10 mm to provide good stent radiopacity. Ideally the ratio of the width 15 to the thickness 25 should be less than 1.0 and preferably less than 0.8. For a coronary stent, the nominal strut width 15 would typically be 0.08 mm and the nominal wall thickness 25 would typically be 0.12 mm. The combination of thin strut width 15 and thick wall thickness 25 will allow the "N" link 14 to easily lengthen and shorten for increased stent flexibility while making the "N" link 14 relatively stiff with respect to bulging inward into the lumen of the stent 10. This stiffness will enhance the ability of the "N" link 14 to push outward against plaque in a coronary artery after the stent 10 is deployed. In addition to improved flexibility, the thin width 15 of the "N" link 14 will allow it to stretch during stent expansion to reduce the foreshortening of the stent 10.

Figure 4:
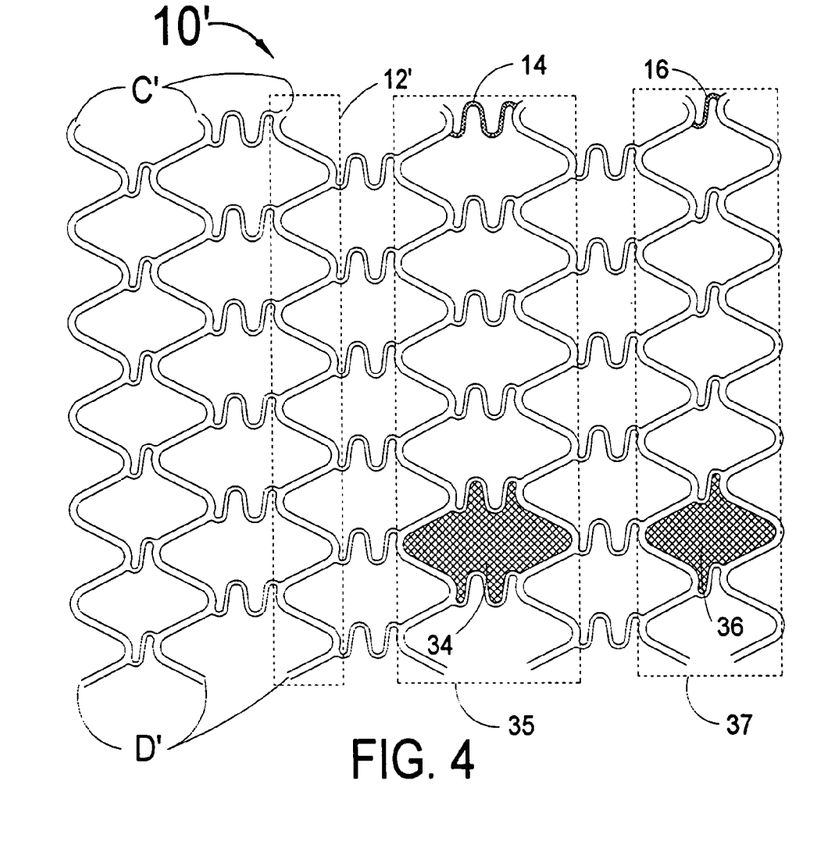
FIG. 4 shows a flat, layout, 2-dimensional plan view of the cylindrical stent of FIG. 2 as it would appear after deployment.

FIG. 4 is a 2-dimensional representation of the cylindrical stent 10' after deployment; i.e., after radially outward expansion. It should be clearly understood that the stent 10' is in fact cylindrical in shape, which cylindrical shape would be obtained by rolling the flat configuration of FIG. 4 into a cylinder with the top points "C" joined to the bottom points "D". FIG. 4 shows how the stent 10 of FIG. 2 would appear after expansion. FIG. 4 also shows the deployed structural cells 36 having on their perimeter two of the "J" links 16 and the deployed special expandable cells 34 having on their perimeter two of the flexible "N" links 14.

It should be noted that circumferentially extending sets of cells 34 and 36 are formed into ring-like, circumferential, cylindrical sections with (in this case) exactly six cells per cylindrical segment. Typically a multi-cell stent would have at least three cells per circumferential cylindrical section. The stent 10' has exactly two cylindrical sections 37 of structural cells 36 and four cylindrical sections 35 of expandable cells 34.

Prior to deployment, the "N" links 14 of the stent 10 of FIG. 2 provide greatly enhanced longitudinal flexibility for the stent 10. This allows for easier placement of the stent 10 through highly curved coronary arteries.

FIGS. 2 and 4 clearly show that the "J" link 16 is much shorter in length as compared to the "N" link 14. Therefore, the perimeter length of the cells 34 is longer that the perimeter length of the cells 36. Therefore, as compared to a cell 36, not only is it easier to expand a cell 34 by placing a balloon through that cell for side branch access and inflating that balloon to a high pressure, but each cell 34 is also expandable to a greater diameter as compared to any cell 36. Since only the center section of the stent 10' would be placed over the ostium of an arterial side branch, "J" links 16 are used only between the end pairs of sets of strut members 12'. Having structural cells 36 at the ends of the stent 10' will increase the radial strength of the stent 10' at the ends. This has merit because the ends of a stent tend to be weaker than the center as the sets of strut members 12' at the end of the stent 10' are connected to only one adjacent set of strut members 12'. Having expandable cells 34 in the central region (with each cell having a longer perimeter length) of the stent will allow use of a second balloon to create an opening in the stent 10' at the site of a stent side branch.

Figure 5:
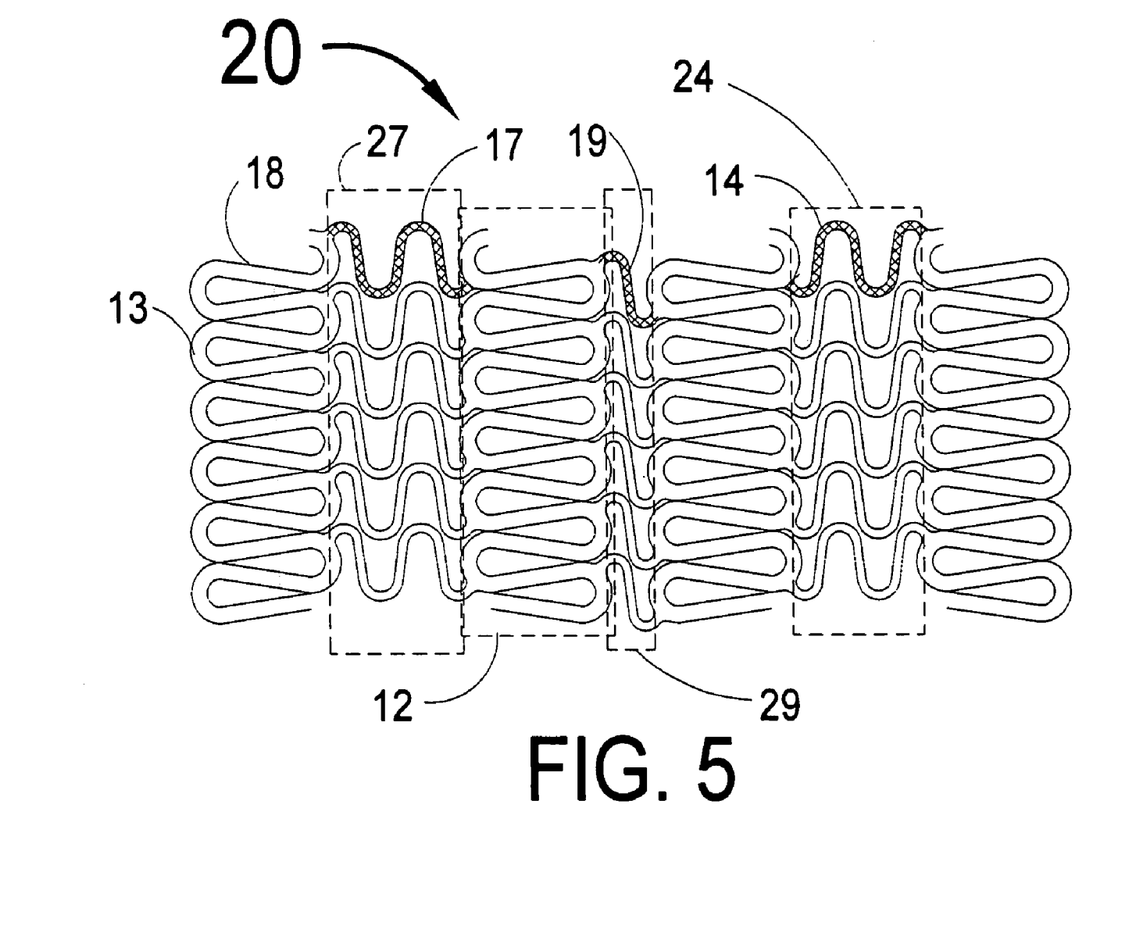
FIG. 5 illustrates another embodiment of the present invention having an alternative arrangement of the "N" and "J" links between sets of strut members, represented as a flat, layout, 2-dimensional plan view.

FIG. 5 shows the stent 20 which is another embodiment of the present invention in its crimped, pre-deployed state as it would appear if it were cut longitudinally and then laid out into a flat, 2-dimensional configuration. The stent 20 like the stent 10 of FIG. 2 has curved end struts 13 and diagonal struts 18 with each set of strut members 12 connected by sets of flexible links 19, 24 or 27. In this embodiment, three different types of flexible links are used. A set of "N" links 24 comprising six circumferentially spaced "N" links 14 and a set of inverted "N" links 27 comprising six circumferentially spaced inverted "N" links 17 each connect to adjacent sets of strut members 12 at the ends of the stent 20. A set of inverted "N" links 29 comprising six circumferentially spaced inverted "J" links 19 are used to connect the adjacent sets of strut members 12 in the center of the stent 20. The shape of the "N" links 14 and inverted "N" links 17 facilitate the links' ability to lengthen and shorten as the stent bends around a curve during delivery into the human body. This ability to lengthen and shorten helps to prevent the sets of strut members from being pushed or pulled off the balloon during delivery into the body and is particularly applicable to short stents which tend to have relatively poor stent retention onto an inflatable balloon. The stent 20 with its greater strength at its central region would advantageously be used for comparatively short stenoses that have a tough, calcified central section. It should also be understood that a regular "J" link could be used for the stent 20 in place of the inverted "J" link 19.

Figure 6:
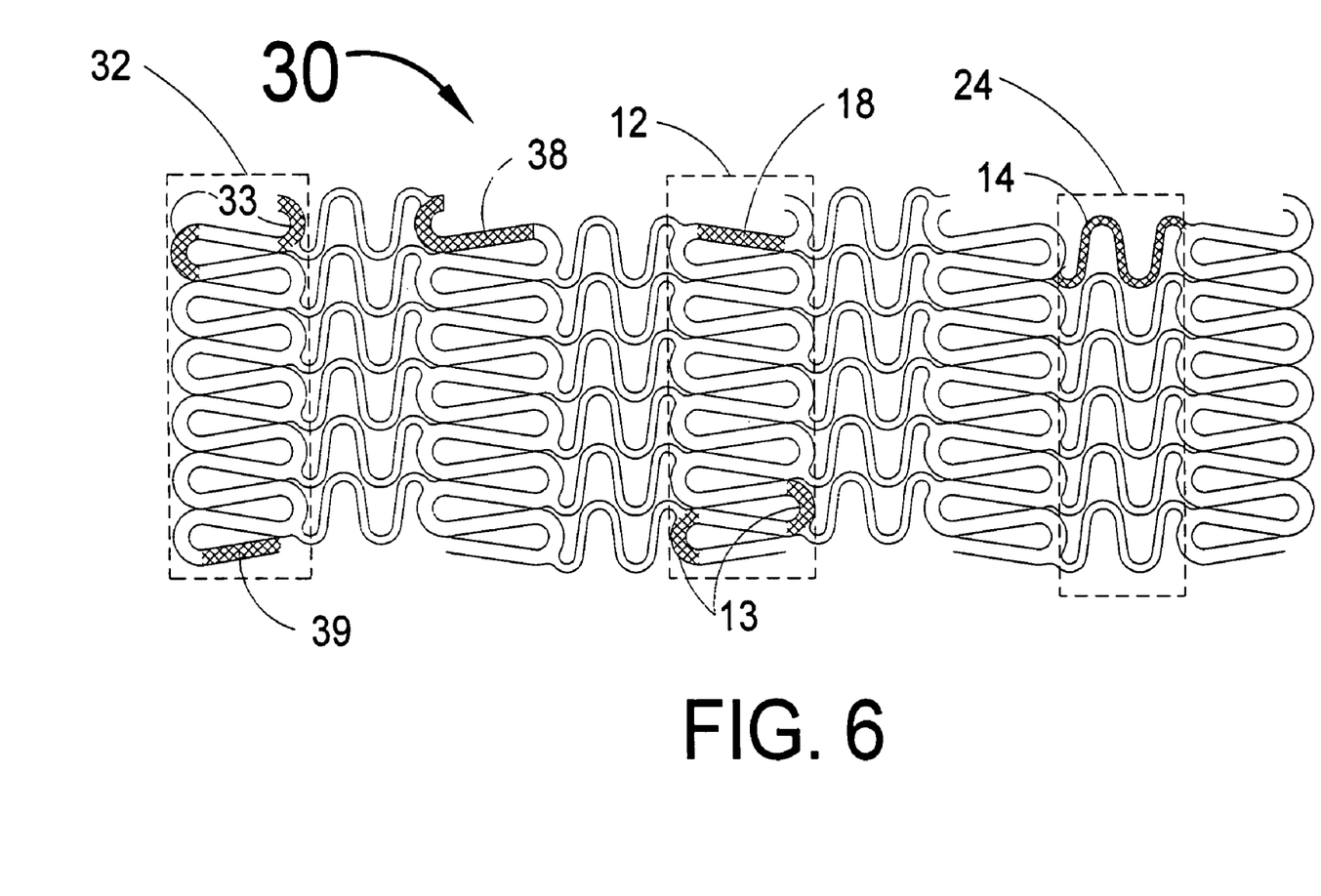
FIG. 6 illustrates another embodiment of the present invention having a single type of flexible connecting link with the stent being represented by a flat, layout, 2-dimensional plan view.

FIG. 6 shows yet another embodiment of the present invention which is a stent 30 in its crimped, pre-deployed state as it would appear if it were cut longitudinally and then laid out into a flat, 2-dimensional configuration. The stent 30 comprises end sets of strut members 32 located at each end of the stent 30 and three center sets of strut members 12 connected each to the other by sets of flexible "N" links 24. The end sets of strut members 32 consist of curved end struts 33 and diagonal struts 39. The center sets of strut members 12 located longitudinally between the end sets of strut members 32 consist of curved end struts 13 and diagonal struts 18. One curved end strut (such as the curved end strut 13) that is joined at a junction point to one diagonal strut (such as the diagonal strut 18) is defined herein as a strut element (such as the strut element 38 of FIG. 6). In this embodiment, the diagonal struts 39 of the end sets of strut members 32 are shorter in length than the diagonal struts 18 of the central sets of strut members 12. The shorter diagonal struts 39 will increase the post-expansion strength of the end sets of strut members 32 as compared with the central sets of strut members 12. The stent 30 also differs from the stent 10 of FIG. 1 and the stent 20 of FIG. 3 in that all of the adjacent sets of strut members 32 or 12 are connected with "N" links 14. The stent 30 has no "J" links 16 as shown in the stent 10 of FIG. 2. Also as shown in FIG. 2, each "N" link 14 has three generally circumferentially extending segments 19 that run in an approximately circumferential direction. When crimped onto a balloon, a stent's ability to avoid sliding on the balloon is related to the ratio of circumferentially placed metal segments to longitudinally extending segments. The three circumferentially extending segments 19 of the "N" link 14 provide a significant amount of circumferentially placed metal to assist in stent retention. In addition, the end set of strut members 32 will stay crimped down on a balloon even as the balloon catheter is repeatedly advanced around a sharp bend because the "N" links 14 can easily lengthen and shorten to adjust the stent length on the outside and inside of the bend respectively.

Figure 7:
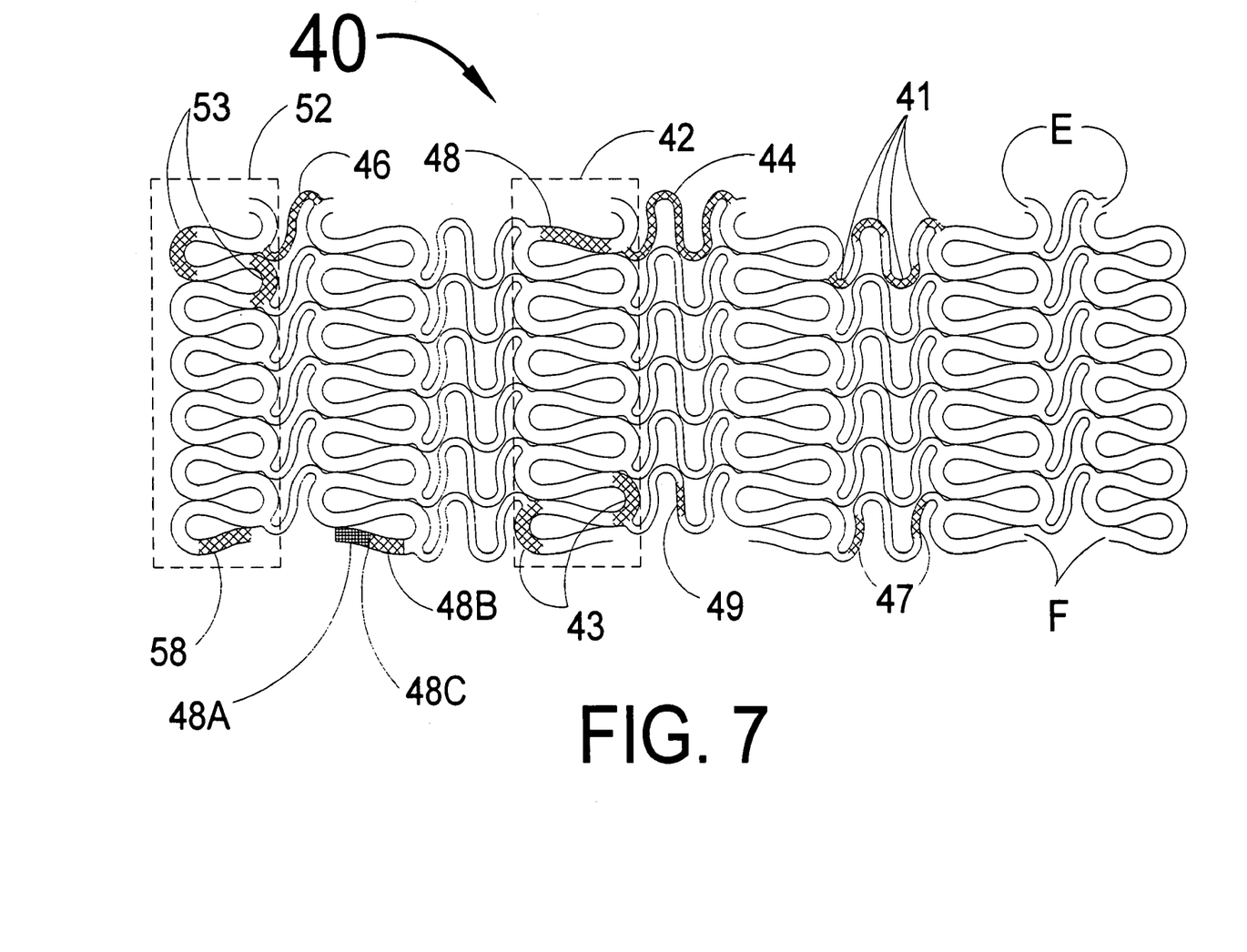
FIG. 7 illustrates another embodiment of the present invention which has flexible sine wave links having curved segments to allow closer spacing of the sets of strut members thereby producing a relative reduction in post-expansion cell size and increase in stent radial rigidity.

FIG. 7 shows the stent 40 which is still another embodiment of the present invention. The stent 40 is shown in its crimped, pre-deployed state as it would appear if it were cut longitudinally and then laid out into a flat, 2-dimensional configuration. It should be clearly understood that the stent 40 is in fact cylindrical in shape, which cylindrical shape would be obtained by rolling the flat configuration of FIG. 7 into a cylinder with the top points "E" joined to the bottom points "F". The stent 40 is typically fabricated by laser machining of a cylindrical, stainless steel tube.

A central set of strut members 42 is a cylindrical, closed, ring-like section of the stent 40 consisting of six pairs of longitudinally separated curved end struts 43 connected by curved diagonal struts 48. Each of the curved diagonal struts 48 has two connected curved segments 48A and 48B that are fixedly attached at an inflection point 48C. A curved diagonal 48 has an advantage over a straight diagonal 18 (of FIG. 2) because, for the expansion of the stent to the same diameter into an artery, the strain in the metal of each set of strut members is reduced. Every curved end strut 43 of a central set of strut members 42 is attached to either a connecting link which is an sine wave link 44 or a curved "J" link 46. The stent 40 also has two end sets of strut members 52 comprising six pairs of longitudinally separated curved end struts 53 connected by curved diagonal struts 58. The central set of strut members 42 is situated longitudinally between the two end sets of strut members 52. Each of the two end sets of strut members 52 is joined to a central set of strut members 42 by a multiplicity of individual curved "J" links 46. Each central set of strut members 42 is joined to an adjacent central set of strut members 42 by a multiplicity of individual sine wave links 44. In this embodiment, half of the curved end struts 53 of the end set of strut members 52 are attached to the curved "J" links 46, the other half of the curved end struts 53 are at the extreme ends of the stent 40. The stent 40 has curved diagonal struts 58 of the end sets of strut members 52 that are shorter than the curved diagonal struts 48 of the central sets of strut members 42. Shorter diagonal struts enhance the post-expansion radial strength of the end sets of strut members 52 as compared to the central sets of strut members 42. This is desirable as the end sets of strut members 52 are only connected to adjacent sets of strut members 42 on one side.

As seen in FIG. 7, the sine wave links 44 consist of a set of four generally longitudinally extending curved segments 41 at the top and bottom, a straight circumferential section 49 at the center and two curved circumferential segments 47 which run parallel to the curved end struts 43 of the sets of strut members 42. The stent 40 differs from the stent 10 of FIG. 2 as the sine wave links 44 of the stent 40 replaces the three generally straight circumferential segments 19B of the "N" link 14 of the stent 10 with two curved circumferential segments 47 and one generally straight segment 49. Use of the curved circumferential segments 47 creates a reduced longitudinal separation of the adjacent sets of strut members 42 connected by the sine wave links 44 as compared to the separation of the sets of strut members 12 connected by the "N" links 14 of FIG. 2. A reduced longitudinal separation of adjacent sets of strut members 42 will result in a smaller expanded cell size for the stent 40 as compared to the stent 10, all other dimensions being equal. This provides slightly increased radial rigidity when the stent 40 is deployed because there are more sets of strut members 42 per unit length of the stent 40 as compared with the number of sets of strut members 12 of the stent 10. The curved circumferential segments 47 are designed to allow the laser used in cutting the stent 40 the minimum slot width between the outside of the curved strut 43 and the inside of the thin curved section 47. The curved "J" links 46 of the stent 40 also have a similar curved shape parallel to the curved struts 43 or the curved struts 53.

Figure 8:
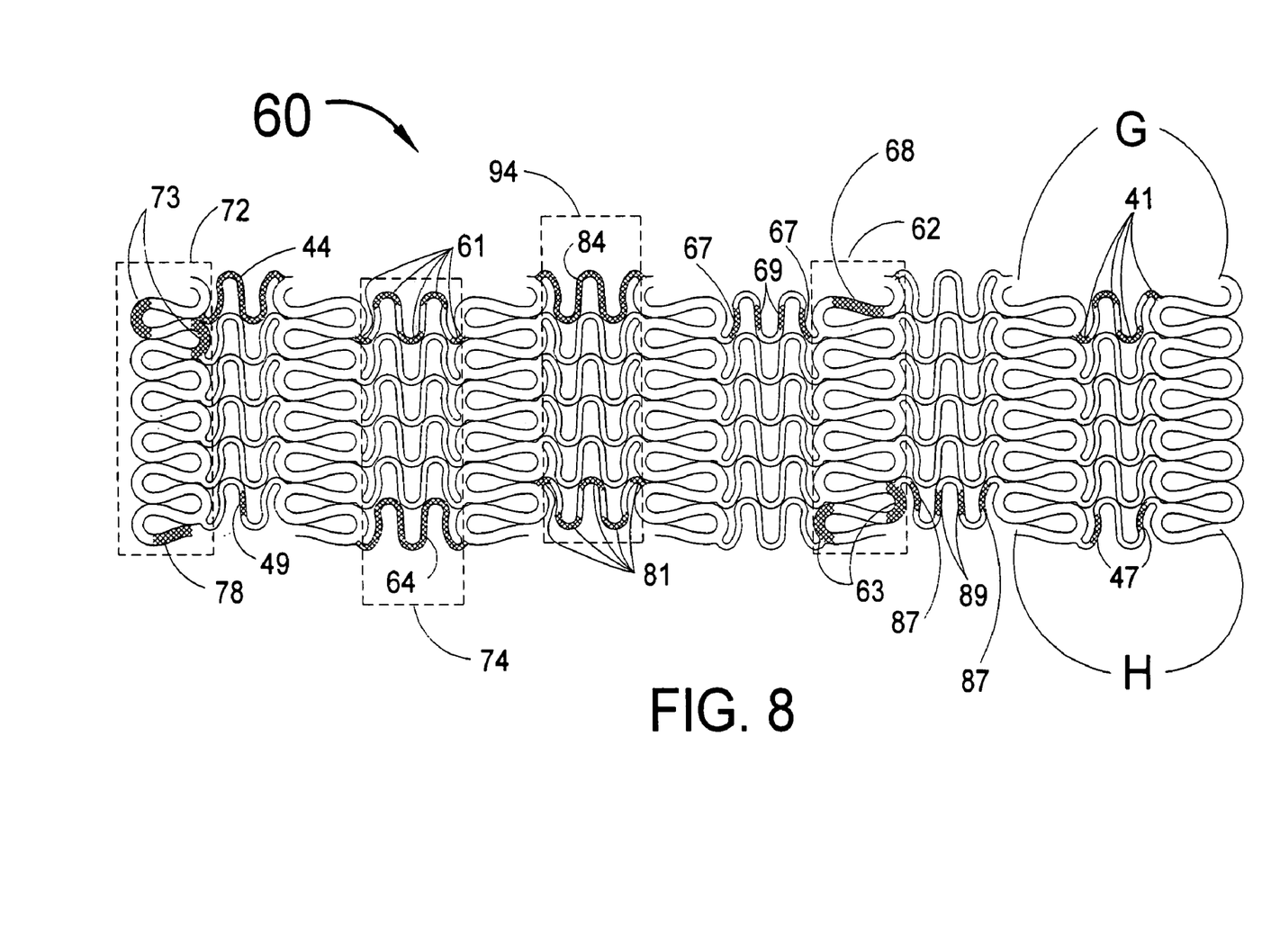
FIG. 8 illustrates still another embodiment of the present invention having the flexible sine wave links of FIG. 7 for connecting the end pairs of sets of strut members with "M" or "W" shaped links to connect centrally located sets of strut members.

The stent 60 shown in FIG. 8 is a flat layout of an ultra-flexible embodiment of the present invention shown in its crimped pre-deployed state as it would appear if it were cut longitudinally and then laid out into a flat, 2-dimensional configuration. It should be clearly understood that the stent 60 is in fact cylindrical in shape, which cylindrical shape would be obtained by rolling the flat configuration of FIG. 8 into a cylinder with the top points "G" joined to the bottom points "H". The stent 60 is typically fabricated by laser machining of a cylindrical, stainless steel tube.

A central set of strut members 62 is a cylindrical, closed, ring-like section of the stent 60 consists of a set of connected, curved end struts 63 and curved diagonal struts 68. Every curved end strut 63 of a central set of strut members 62 is attached to a connecting link which is either a flexible ""M" link 64 or a "W" link 84. The stent 60 also has two end sets of strut members 72 consisting of a set of connected, curved end struts 73 and curved diagonal struts 78. In this embodiment, half of the curved end struts 73 of the end set of strut members 72 are attached to sine wave links 44, the other half of the curved end struts 73 are at the extreme ends of the stent 60. The curved diagonal struts 78 of the end sets of strut members 72 are shorter than the curved diagonal struts 68 of the central sets of strut members 62. Shorter diagonal struts enhance the post-expansion radial strength of the end sets of strut members 72 as compared to the central sets of strut members 62. This is desirable as the end sets of strut members 72 are only connected to adjacent sets of strut members 62 on one side and are therefore naturally weaker.

Each sine wave link 44 of the stent 60 has four curved longitudinally extending segments 41, two curved circumferentially extending segments 47 and one generally straight circumferentially extending segment 49.

The stent 60 has two sets of flexible links 74 each consisting of six individual flexible M" links 64. The "M" links 64 consist of a set of five generally longitudinally extending curved segments 61 at the top and bottom, two generally straight circumferentially extending segments 69 in the center and two curved circumferentially extending segments 67 which run parallel to the curved end struts 63 of the sets of strut members 62. The stent 60 differs from the stent 40 of FIG. 7 in that the "M" links 64 of the stent 60 have one more generally longitudinally extending curved segment 61 and one more generally straight circumferential segment 69 as compared to the sine wave links 44 of the stent 40.

The stent 60 has two sets of flexible links 94 each consisting of six individual flexible links "W" links 84. The "W" links 84 comprise a set of five generally longitudinally extending curved segments 81 at the top and bottom, two generally straight circumferential segments 89 in the center and two curved circumferentially extending segments 87 which run generally parallel to the curved end struts 63 of the sets of strut members 62. The "W" link 84 is the mirror image of the "M" link 64. It is obvious that any flexible link described herein could be connected at the center of any of the curved end segments of the set of strut members that are described herein.

Figure 9:
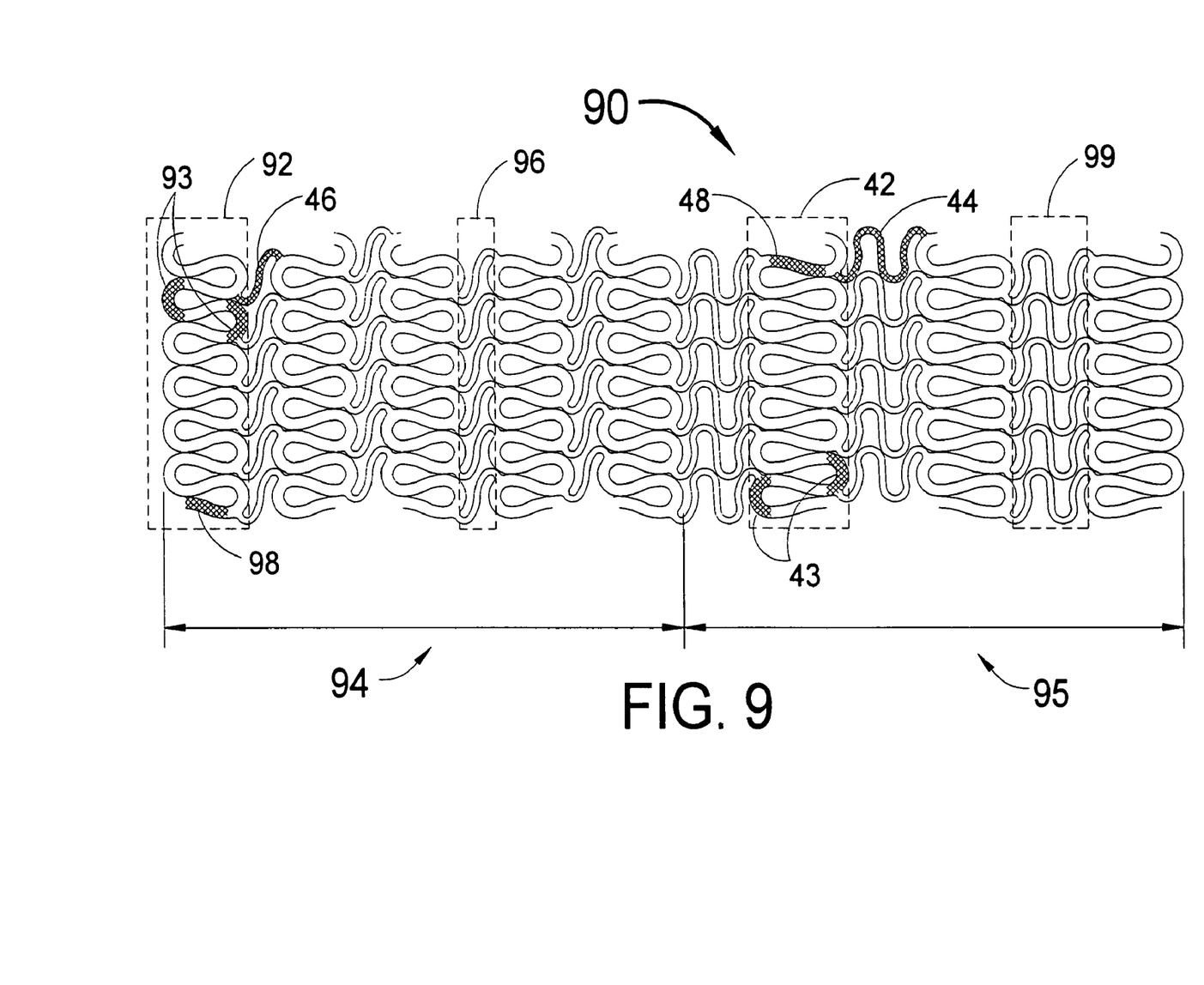
FIG. 9 illustrates an embodiment of the present stent invention adapted for implantation at the ostium of a vessel, the stent being shown as a flat, layout, 2-dimensional plan view; the proximal section of the stent having only "J" links and the distal section having only flexible sine wave links.

The stent 90 of FIG. 9 is still another embodiment of the present invention shown in its crimped pre-deployed state as it would appear if it were cut longitudinally and then laid out into a flat, 2-dimensional configuration. The stent 90 is adapted to be placed at the ostium of a vessel of the human body such as a renal artery. The stent 90 has a proximal section 94 and a distal section 95. The proximal section 94 is constructed from five shortened sets of strut members 92 connected by sets of flexible curved "J" links 96. Each set of strut members 92 consists of six pairs of curved end struts 93 connected by curved diagonal struts 98. Each set of flexible curved "J" links 96 consists of six circumferentially spaced curved "J" links 46 identical to the "J" links 46 of the stent 40 of FIG. 7.

The distal section 95 of the stent 90 is constructed from three sets of strut members 42 connected by sets of flexible sine wave links 99. Each set of strut members 42 consists of six pairs of curved end struts 43 connected by curved diagonal struts 48. Each set of flexible sine wave links 99 consists of six circumferentially spaced sine wave links 44 identical to the sine wave links 44 of the stent 40 of FIG. 7.

The distal section 95 of the stent 90 will be more longitudinally flexible than the proximal section 94 because of the presence of the sine wave links 44. After being deployed, the proximal section 94 will be radially stronger than the distal section 95 for two reasons. First, the proximal section 94 has five strong sets of strut members 92 over approximately the same longitudinal length as the three sets of strut members 42 of the distal section 95. Second, each strong set of strut members 92 has shorter curved diagonals 98 as compared to the curved diagonals 48 of the sets of strut members 42. Shorter diagonals produce increased radial strength for a deployed stent. It should be understood that the proximal section 94 that would be placed near the ostium of an artery should have greater radial strength to prevent the ostium from closing. Also, the distal section 95 should have increased flexibility so as to more easily make the turn to enter the ostium of a vessel such as the renal artery.

Although the descriptions herein show individual, flexible "J", curved "J", "M", "N", "W" and sine wave links in specific configurations, it is envisioned that any combination of these flexible links or inverted flexible links can be utilized. Similarly, although end sets of strut members having shorter diagonals have been shown in FIGS. 6, 7 and 8, it is envisioned that sets of strut members having shorter diagonals might be used at any position along the length of the stent. It is also envisioned that any of the individual flexible links described herein could be connected to a center point of the adjacent curved end strut. For example in FIG. 2, the attachment point 55 at the end of the "N" link 14 could be connected to the center point 51 of the curved end strut 13.

Although the stents described herein would principally be used in arteries, they could also be applied to other types of vessels of the human body such as veins, vascular graphs, bronchial tubes in the lung or the bile duct in the liver.

To clearly define the various shapes of the flexible links that are single, undulating structures that extend generally in a longitudinal direction, the following definitions shall apply:

1. "J" link: a generally longitudinally extending flexible structure having two generally longitudinally extending curved segments that are joined by one circumferentially extending segment as shown by element 16 of FIGS. 2 and 4.

2. Inverted "J" link: the mirror image of the "J" link defined in 1 above as shown by element 19 of FIG. 5.

3. "N" link: a generally longitudinally extending flexible structure having four generally longitudinally extending curved segments that are joined by three generally straight circumferentially extending segments of approximately equal length; as shown by the element 14 of FIGS. 2, 3, 4, 5, and 6.

4. Inverted "N" link: the mirror image of the "N" link as defined in 3 above; as shown by element 17 of FIG. 5.

5. Sine-wave link: a flexible link that has two curved generally circumferentially extending end segments and one generally straight circumferentially extending segment that is situated between the curved segments instead of the three generally straight circumferentially extending segments of the "N" link. The sine wave link is illustrated as element 44 of FIGS. 7, 8 and 9.

6. "M" link: a generally longitudinally extending flexible structure having five generally longitudinally extending curved segments that are connected together by four generally circumferentially extending segments of approximately equal length; as shown by element 64 of FIG. 8.

7. "W" link: same as 6 above except it is turned upside down; as shown by element 84 of FIG. 8.

Various other modifications, adaptations, and alternative designs are of course possible in light of the above teachings. Therefore, it should be understood at this time that within the scope of the appended claims, the invention can be practiced otherwise than as specifically described herein.

As further seen in FIGS. 2 and 4–9, but most typically in FIG. 8, the flexible links 44 and the curved end segments 73 are arranged in such a fashion so that the stent does not flare upon arterial traversal or expansion. First, links 44 are placed so that a line connecting their proximal and distal ends lie transverse to the longitudinal axis of the stent. Second, the outermost curved segments 41 of the links 44 (that is, where these segments are attached to a curved segment 63, 73 respectively) are joined to these segments at a point where the tangent of the curved end segment is at an acute angle to the longitudinal axis of the stent when taken in the direction of the flexible link 44. The reduced flaring upon expansion created by this structure allows the operator to place the stent by direct stenting, without pre-dilatation of an arterial stenosis. This arrangement may be achieved on each flexible link of the stent along its length.

What is claimed is:

1. A stent in the form of a generally tubular structure having a longitudinal axis, the stent comprising;

a plurality of circumferential sets of strut members that extend in a generally circumferential, ring-like pattern around the stent's longitudinal axis with each circumferential set of strut members comprising a plurality of curved end struts, the curved end struts being substantially curved across their entire length;

a plurality of flexible links with each flexible link being fixedly attached to two adjacent circumferential sets of strut members and each flexible link having a proximal end and a distal end with a line drawn through the proximal and distal ends of the flexible link lying transverse to the stent's longitudinal axis, each flexible link having at least four generally longitudinal extending curved segments that each have a proximal end and a distal end with a line joining the proximal end and distal end of each curved segment being generally parallel to the stent's longitudinal axis, the curved segments being connected together in series by three generally circumferentially extending segments of approximately equal length; and the stent being further characterized by having the outermost curved segment of each flexible link connected to each curved end strut at a point thereon, the tangent to the curved end segment at which point being at an acute angle with respect to the stent's longitudinal axis as taken in the direction of the curved end strut that is opposite the curved end strut onto which the outermost curved end segment is attached.

2. The stent of claim 1 wherein the width of the each flexible link is less than the width of each curved end strut.

3. The stent of claim 1 wherein the ratio of thickness to width of each flexible link is greater than 1.0.

4. The stent of claim 1 wherein the link is formed from stainless steel.

5. The stent of claim 1 wherein the link is formed in the shape of a letter "N".

* * * * *